US007277740B2

(12) United States Patent
Rohleder et al.

(10) Patent No.: US 7,277,740 B2
(45) Date of Patent: Oct. 2, 2007

(54) ANALYSIS SYSTEM FOR REAGENT-FREE DETERMINATION OF THE CONCENTRATION OF AN ANALYTE IN LIVING TISSUE

(75) Inventors: Daniel Rohleder, Mannheim (DE); Wolfgang Petrich, Bad Schonborn (DE); Alexa Nagel, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 343 days.

(21) Appl. No.: 10/800,215

(22) Filed: Mar. 12, 2004

(65) Prior Publication Data

US 2004/0260162 A1 Dec. 23, 2004

(30) Foreign Application Priority Data

Mar. 15, 2003 (DE) ................................ 103 11 452

(51) Int. Cl.
*A61B 5/00* (2006.01)
(52) U.S. Cl. ........................................ 600/316; 600/342
(58) Field of Classification Search ................ 600/327, 600/341, 342, 310, 316, 322
See application file for complete search history.

(56) References Cited

U.S. PATENT DOCUMENTS

| 3,966,300 | A | * | 6/1976 | Bernsee ....................... 385/142 |
| 4,201,222 | A | | 5/1980 | Haase |
| 4,925,268 | A | * | 5/1990 | Iyer et al. ..................... 385/12 |
| 5,000,901 | A | | 3/1991 | Iyer et al. |
| 5,005,576 | A | | 4/1991 | Gunther |
| 5,127,077 | A | | 6/1992 | Iyer et al. |
| 5,143,066 | A | | 9/1992 | Komives et al. |
| 5,173,432 | A | | 12/1992 | Lefkowitz et al. |
| 5,348,003 | A | * | 9/1994 | Caro .......................... 600/310 |
| 5,423,320 | A | | 6/1995 | Salzman et al. |
| 5,434,084 | A | | 7/1995 | Burgess, Jr. |
| 5,481,113 | A | | 1/1996 | Dou et al. ................ 250/341.1 |

(Continued)

FOREIGN PATENT DOCUMENTS

DE 100 27 100 C2 12/2001

(Continued)

OTHER PUBLICATIONS

Shim, MG, "Assessment of Ex vivo and In vivo Near-Infrared Raman Spectroscopy for the Classification of Dysplasia Within Barrett's Esophagus." Biomedical Spectroscopy: Vibrational Spectroscopy and Other Novel Techniques, Proceedings of SPIE vol. 3918 (2000), 114-119.

(Continued)

*Primary Examiner*—Eric F Winakur
(74) *Attorney, Agent, or Firm*—Woodard, Emhardt, Moriarty, McNett & Henry LLP

(57) ABSTRACT

The present invention is generally directed towards a system for reagent-free determination of the concentration of an analyte in vivo. The system comprises a light transmitter for generating monochromatic primary light, a scattered-light percutaneous sensor which includes an inbound light guide and a detection light guide, a wavelength-selective detection device that is connected to the detection light guide for detection of Raman-scattered components of the secondary light and an evaluation device for determining the concentration of the analyte from the Raman-scattered components of the secondary light.

32 Claims, 4 Drawing Sheets

U.S. PATENT DOCUMENTS

| | | | | |
|---|---|---|---|---|
| 5,553,616 | A | * 9/1996 | Ham et al. | 600/316 |
| 5,835,649 | A | 11/1998 | Turner et al. | 385/31 |
| 6,151,522 | A | 11/2000 | Alfano et al. | 600/473 |
| 6,167,290 | A | * 12/2000 | Yang et al. | 600/322 |
| 6,370,406 | B1 | * 4/2002 | Wach et al. | 600/310 |
| 6,377,828 | B1 | * 4/2002 | Chaiken et al. | 600/316 |
| 6,584,335 | B1 | * 6/2003 | Haar et al. | 600/322 |

FOREIGN PATENT DOCUMENTS

| | | |
|---|---|---|
| WO | WO97/19344 | 5/1997 |
| WO | WO97/34175 | 9/1997 |
| WO | WO97/42868 | 11/1997 |
| WO | WO99/07277 | * 2/1999 |
| WO | WO 02/07585 A2 | * 1/2002 |

OTHER PUBLICATIONS

Petrich, W., "Mid-Infrared and Raman Spectroscopy for Medical Diagnostics". Applied Spectroscopy Reviews, 36(2&3), 181-237 (2001).

* cited by examiner

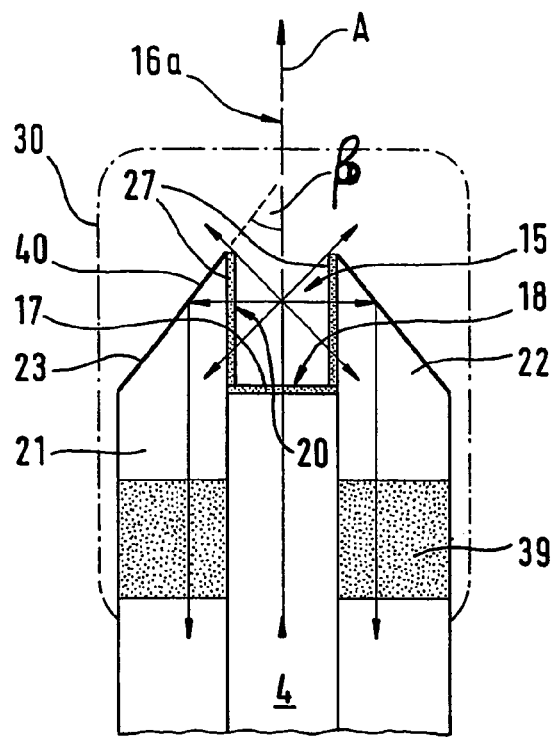
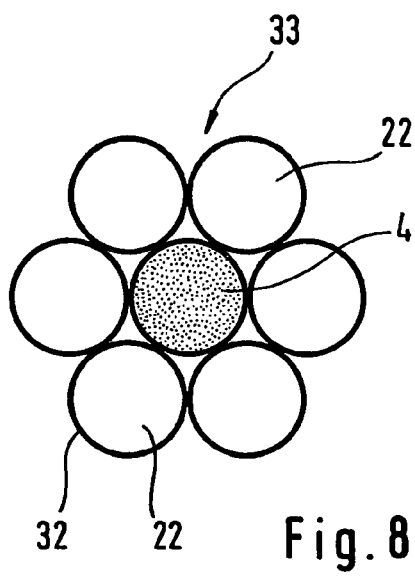
Fig. 7
Fig. 8
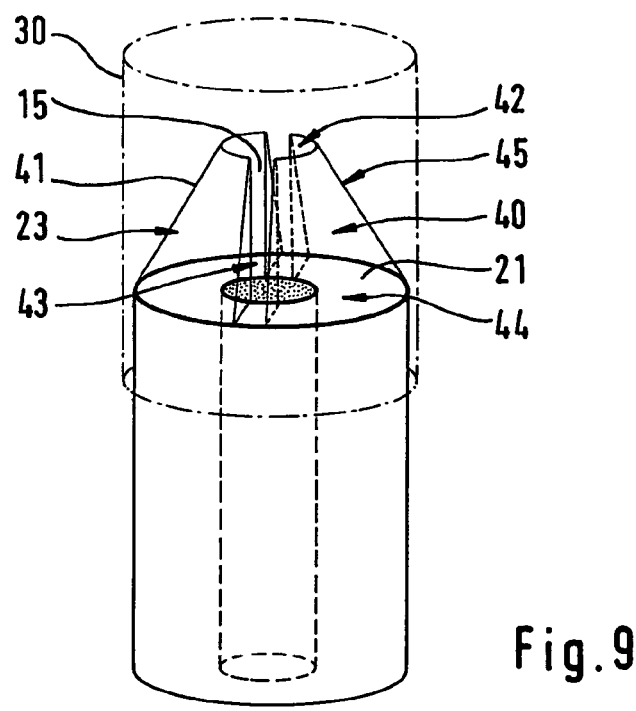
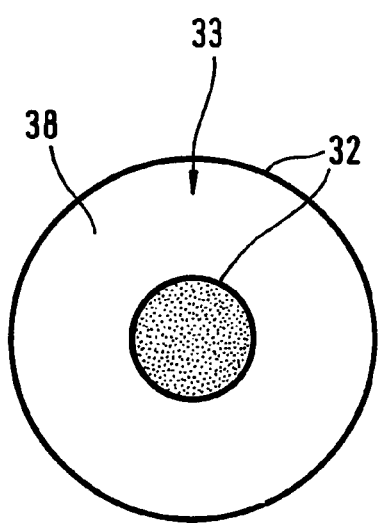
Fig. 9
Fig. 10

ANALYSIS SYSTEM FOR REAGENT-FREE DETERMINATION OF THE CONCENTRATION OF AN ANALYTE IN LIVING TISSUE

PRIORITY CLAIM

This application claims priority to German Application Number DE 103 11 452.1 filed Mar. 15, 2003.

TECHNICAL FIELD

The invention relates to a system for the determination of the concentration of an analyte percutaneously in vivo.

BACKGROUND

Medically relevant analytes to which the invention refers include, for example, cholesterol, triglycerides, uric acid, urea, proteins (in particular albumin), globulins, hematocrit and hemoglobin. Glucose is an especially important analyte, because quantitative analysis of glucose is the prerequisite for diabetics to adapt their insulin injections to their actual needs and thereby prevent fluctuations in blood sugar level outside of a relatively narrow normal range. It has been demonstrated in extensive studies that serious long time consequences of diabetes mellitus (e.g., blindness due to retinal damage) can be largely prevented if such close monitoring of blood sugar level is ensured. This requires, however, very frequent or, if possible, continuous determination of the glucose concentration in vivo. The following discussion makes reference to glucose as an example of an analyte, but this must not be understood as restricting the general applicability of the invention, which is suitable for various analytes.

The concentration of analytes in body fluids is determined for medical purposes mainly by using reagents. A sample of a body fluid (in particular blood) is taken and analyzed in vitro in the laboratory. Although these methods have been improved continuously, and small, easy-to-handle analysis systems have become available in the meantime, it is a disadvantage that a blood sample must be taken for each individual analysis and that continuous measurement is impossible.

As a result, observation of glucose levels is incomplete and discontinuous. For hygienic reasons (risk of infection at the puncture site) and psychological reasons (pain due to the puncture) only relatively few analyses can reasonably be performed each day. This increases the risk of both hypoglycemia and hyperglycemia as well as irreversible long-term damage. In contrast, a measuring system that determines blood glucose levels continuously could provide prompt warning of critical hyper- or hypoglycemic levels and could supply the necessary data for accurate dosing of insulin.

Numerous proposals have already been made for continuous quantitative analysis in vivo. For example, it has been proposed that interstitial fluid be removed continuously from the body and pumped to a measuring system outside of the body, where the glucose concentration would be determined electrochemically (WO 97/42868). However, this method is very complex and is suitable only for short usage periods (a few days) because of the consumption of reagents and perfusion solution.

Another method which also requires reagents is described in WO 97/19344, where the chemicals needed for reacting with glucose are introduced into the patient's body. This results in problems with reaction products, which may be toxic. Additionally, the glucose concentration is influenced by the measurement itself, which could thereby corrupt the measurement results.

Numerous proposals for reagent-free in-vivo analysis have been based on optical adsorption spectroscopy. For example, WO 99/07277 describes a device for in-vivo analysis, comprising a measuring probe with a needle which can be inserted into the skin. Light guides run in the interior of the needle. The analysis is based on the interaction of interstitial fluid, which passes through a perforation in the needle and reaches the lateral surface of the optical fibers, with light being transported in its interior. In particular, the principles of ATR spectroscopy may be used according to this publication.

There are many other examples of methods known for continuous, in particular reagent-free, in-vivo analysis in the human body. Details in this regard can be obtained from the literature citations referenced above. In particular, WO 99/07277, which was mentioned last, contains a detailed discussion of the related art.

An object of the invention is to make available a novel and improved device for reagent-free in-vivo analysis. To achieve this goal, a device for reagent-free in vivo determination of the concentration of an analyte in the body of a patient is proposed, comprising the following components:

a light transmitter for generating monochromatic primary light, a scattered-light percutaneous sensor which
 is insertable into the skin, so that a sensor head at the distal end of the scattered-light percutaneous sensor is located inside the skin,
 includes an inbound light guide in which primary light is conducted through the skin surface into the interior of the body and which has a light irradiation surface at its distal end through which the primary light penetrates from the inbound light guide into a test volume of the tissue of the patient, and
 includes a detection light guide having at its distal end a light receiving surface through which secondary light scattered in the test volume penetrates into the detection light guide and in which the secondary light is conducted through the skin surface out of the patient's body, and a wavelength-selective detection device that is connected to the detection light guide for detection of Raman-scattered components of the secondary light and an evaluation device for determining the concentration of the analyte from the Raman-scattered components of the secondary light.

In Raman spectroscopy, monochromatic primary light of a laser is irradiated into a test volume and the secondary light generated due to scattering in the test volume is spectrally analyzed. In the vicinity of the primary light line, the spectrum includes a line structure that is referred to as Raman-scattered light. Changes of the spectrum of Raman-scattered light are caused by changes in the vibrational and/or rotational states of the scattering molecules and are therefore characteristic of them. Since the intensity of Raman-scattered light correlates with the concentration of the molecules, a quantitative analysis is possible.

To permit adequate resolution of Raman spectral bands, the primary light must have a very narrow bandwidth (i.e. be monochromatic in the technical sense). Laser light is generally used, the emission of a multimode laser being sufficiently monochromatic.

The selection of Raman bands from the scattered light is achieved by a suitable wavelength-selective detection device. Generally, spectrometers which permit spectrally resolved detection of at least a portion of the Raman spectrum are used. In principle, however, other wavelength-selective detection devices may also be used. In particular it may be sufficient to use filters to detect only one or a few bands of the Raman spectrum of the analyte being tested. A plurality of methods and devices are known for this purpose. These may also be used in the context of the present invention.

Raman spectroscopy has gained considerable importance in chemical analysis. However, difficult problems are caused by the fact that the scattered secondary light also contains other light components, in addition to Raman-scattered light, which have a much greater intensity.

The primary light required for excitation of the Raman-scattered light is also scattered elastically (Rayleigh scattering) in the test object. The intensity of this Rayleigh scattering in a turbid medium is typically about $10^6$ times the intensity of the Raman-scattered light.

Additional interference is caused in practice by primary light which falls onto the detector, e.g., due to reflection on parts of the apparatus. Its intensity is several orders of magnitude higher than that of the Raman-scattered light. For example, particularly problematical interference is caused when the specimen to be analyzed contains fluorescent molecules. The interference due to Rayleigh-scattered light and due to superimposed primary light has a wavelength different from the Rayleigh-scattered light and therefore can be reduced by using a suitable filter. In contrast, fluorescent light largely coincides with the Raman bands and therefore cannot be separated out by filtering. In addition, there is interfering light generated in fiber-optic guides (light guide fibers) due to the fact that Raman scattering and fluorescence also occur in the fiber.

Because of these major problems, Raman spectroscopy was originally used only in very clear sample materials which are free of scattering centers. This restriction has been partly overcome due to the availability of lasers as very sharply monochromatic light sources and due to improved filter techniques. There remain, however, some very major problems with the use of Raman spectroscopy in the analysis of biological materials, as is also apparent from prior art experiments with biological samples.

U.S. Pat. No. 5,481,113 relates to the analysis of biological materials by means of Raman spectroscopy. Previously such measurements had been performed on citrus fruit to investigate their taste properties by analyzing certain components. However, according to the US patent, the earlier method is not suitable for clinical medical tests in vivo because of the excitation wavelength in the visible range of the spectrum (about 500 nm). Interfering fluorescence is said to be generated by the shortwave excitation light. Additionally, the specimen may be damaged due to photolysis. To avoid these problems, the US patent recommends to use primary light with a much greater wavelength in the near infrared range. Due to the lower quantum energy of this light, the occurrence of fluorescence is avoided and therefore the signal-to-noise ratio (S/N ratio) is said to be improved.

The authors of U.S. Pat. No. 6,151,522 come, on the basis of measurements on glucose solutions, to the conclusion that because of the extraordinarily low intensity of the Raman bands, it is practically impossible to determine physiological glucose levels by conventional spontaneous Raman spectroscopy. In experiments conducted by these authors it was impossible to detect a concentration of about 10 mg/mL even with an exposure time of 20 minutes. It is therefore proposed that a significant amplification of the Raman signal can be achieved by using an additional pump laser. The frequency of the pump laser is varied, and an amplified Raman signal ("enhanced Raman") occurs when the difference between the frequency of the pump laser and the frequency of the test laser (which is kept constant) corresponds to the wavenumber of a characteristic Raman line. Thus a Raman spectrum is generated as a function of the excitation frequency. At the same time, the S/N ratio is said to be improved by a frequency-selective method with the help of a lock-in amplifier. Examples of applications include noninvasive analysis of glucose by direct irradiation of a suitable part of the body (e.g., the ear) and identification of cancer cells, (e.g., in the breast, the uterus and the ovaries). However, the technology described in this U.S. patent is very complex and therefore is not suitable for routine continuous analysis of important analytes, in particular glucose.

Another example of using Raman spectroscopy for detection of tissue changes in conjunction with early detection of cancer is described in the following publication:

Martin G. Shim et al. "Assessment of ex-vivo and in-vivo near-infrared Raman spectroscopy for the classification of dysplasia within Barrett's esophagus," in *Biomedical Spectroscopy: Vibrational Spectroscopy and Other Novel Techniques*, A. Mahadevan-Jansen, G. J. Puppels, editors, *Proceedings of SPIE*, vol. 3918 (2000), 114-199.

WO 97/34175 relates to the improvement of various types of scattered-light spectroscopy by means of special designs of the optical fibers used for this purpose. Here again, the fundamental potential of Raman spectroscopy for various industrial and medical applications is emphasized. At the same time, reference is made to the enormous difficulties associated with the fact that the useful signal is extremely weak. Therefore, the measurement technique must be unbelievably efficient. For example, in Raman spectroscopy, it is according to this publication even necessary to eliminate the interfering influence of cosmic radiation (by detecting the singular occurrence of cosmic photons). It is assumed in this document that usually parallel optical fibers are used for scattered-light spectroscopy, one of them being used for input of the primary light (referred to hereafter as the "inbound light guide") and the other being used for transport of scattered light from the test volume to the spectrometer ("detection light guide"). It is explained that the S/N ratio depends to a great extent on the fact that the portion of the specimen "observed" by the detection light guide ("field of view", referred to hereafter as the "detection range") largely corresponds to the range of the sample illuminated by the primary light ("irradiation range") and the fact that the path of the scattered light to the light receiving surface of the detection light guide is as short as possible. To achieve this, optical configurations are proposed in which the detection range detected by the detection light guide (preferably comprising a plurality of optical fibers) is influenced by a reflecting internal surface. Additionally, various filter arrangements are described which serve to eliminate interfering light components that are attributed to Raman scattering or fluorescence occurring in the light guide itself ("silica Raman").

WO 98/55850 describes a similar optical configuration having a reflecting surface (inclined 45° to the axis) at the end of a detection light guide.

As part of the invention, it has been found that Raman spectroscopy can be used successfully for continuous, reagent-free, minimally invasive determination of the concentration of glucose and other analytes in human tissue if the analysis system includes a scattered-light percutaneous sensor which includes an inbound light guide for input of light into a test volume inside the patient's body and a detection light guide by which secondary scattered light in the test volume is detected and conducted out of the body. The scattered-light percutaneous sensor should have a total diameter of at most 2 mm, preferably at most 1 mm and especially preferably at most 0.5 mm. It can therefore be inserted relatively painlessly into the skin at the desired testing site. It is expedient to use an insertion aid with a hollow needle (in the manner of a Peel catheter) that can be inserted into the skin with the scattered-light percutaneous sensor. The insertion aid may then be removed again. This is a known procedure. Suitable insertion aids are available for other purposes (for implantation of catheters in particular).

The quality of the analysis is increased if the preferred embodiments of the invention which are explained hereafter are taken into account.

Depending on the design of the scattered-light percutaneous sensor, the invention is suitable for different localizations of the test volume in the human (or animal) body. In particular, it may be designed in such a manner that it is suitable for insertion into a vein so that the analysis takes place directly in the flowing blood. Preferably, however, the scattered-light percutaneous sensor is designed so that the test volume is, when the percutaneous sensor is inserted into the skin, in the subcutaneous connective tissue and the Raman scattering of the interstitial fluid present there is detected. As part of the invention, it has been found that interstitial fluid is particularly suitable for Raman spectroscopy. First, the glucose concentration in the interstitial fluid follows in good approximation the concentration of glucose in the blood. Secondly, in comparison with blood, it contains far fewer fluorescence molecules, so there is less interference due to fluorescence than in blood.

A further reduction in the interference due to fluorescence is achieved by providing a semipermeable membrane on the distal end of the scattered-light percutaneous sensor, so that the membrane prevents access of macromolecules having a molecular weight above the exclusion limit (molecular cut-off) of the semipermeable membrane to the test volume. The exclusion limit of the membrane is preferably at most 50 kDa, a value of at most 20 kDa being especially preferred.

The wavelength of the primary light used for excitation of Raman scattering is preferably at most 900 nm, values of at most 800 nm or even at most 600 nm being especially preferred. Due to this relatively short wavelength (in contrast with the prior art according to U.S. Pat. No. 5,481,113), the intensity of the Raman-scattered light is greatly increased because the effective cross-section of the Raman scattering increases with the fourth power of the frequency of the excitation light. Because of the reduced fluorescence interference in the context of the invention, this effect may be used to advantage to improve the S/N ratio.

Extremely short wavelengths, in particular in the UV range below 300 nm, are, however, less preferred in the context of the invention, in particular because damage to the tissue must be expected in this range. This wavelength range, which permits generation of excited electronic states, is frequently used for so-called resonance Raman scattering, where the disadvantages of tissue damage must be accepted for the advantage of a higher S/N ratio. Within the context of the invention, spontaneous Raman scattering is preferably used. The particular form of Raman spectroscopy with more than one wavelength of the incident light, as described in U.S. Pat. No. 6,151,522, is not advantageous within the context of the invention.

Finally, improvements are achieved by the fact that the detection range detected by the detection light guide is directed by means of a reflective surface in the direction of the irradiation range illuminated by the primary light. The reflective surface is designed and arranged in such a manner that the primary light emitted from the inbound light guide is not reflected on the light receiving surface of the detection light guide but scattered secondary light is detected by the detection light guide to a greater extent due to the effect of the reflective surface.

The invention achieves a plurality of advantages. In contrast with methods in which light is directed through the skin into subcutaneous layers of tissue, there are no problems due to scattering or absorption at the skin surface. Since the wavelengths of light used are in the visible spectrum or in the infrared range in immediate proximity to the visible spectrum, optical fibers of conventional silicate glass may be used for the light guides. This is in contrast with MIR absorption spectroscopy, in which it is necessary to work with much longer wavelengths and therefore problematical special materials must be used.

The analysis can be performed with practically no delay (real time).

A single puncture is sufficient for a longer period of time. Therefore the invention is also suitable for use by the patient himself ("home monitoring").

Since no reagents are necessary there are no problems with their localization and administration. No toxic residues remain in the body.

Further features and advantages of the invention will become apparent from the following discussion and the accompanying drawings in which:

BRIEF DESCRIPTION OF THE DRAWINGS

FIG. 7; shows a schematic longitudinal section through a third embodiment of a sensor head;

FIG. 8; shows a cross-section through the light guides of the sensor head depicted in FIG. 7;

FIG. 9; shows a schematic perspective view of a fourth embodiment of a sensor head;

FIG. 10; shows a cross-section through the light guides of the sensor head depicted in FIG. 9;

DETAILED DESCRIPTION

The following description of the preferred embodiment is merely exemplary in nature and is in no way intended to limit the invention or its application or uses.

Figure 1:
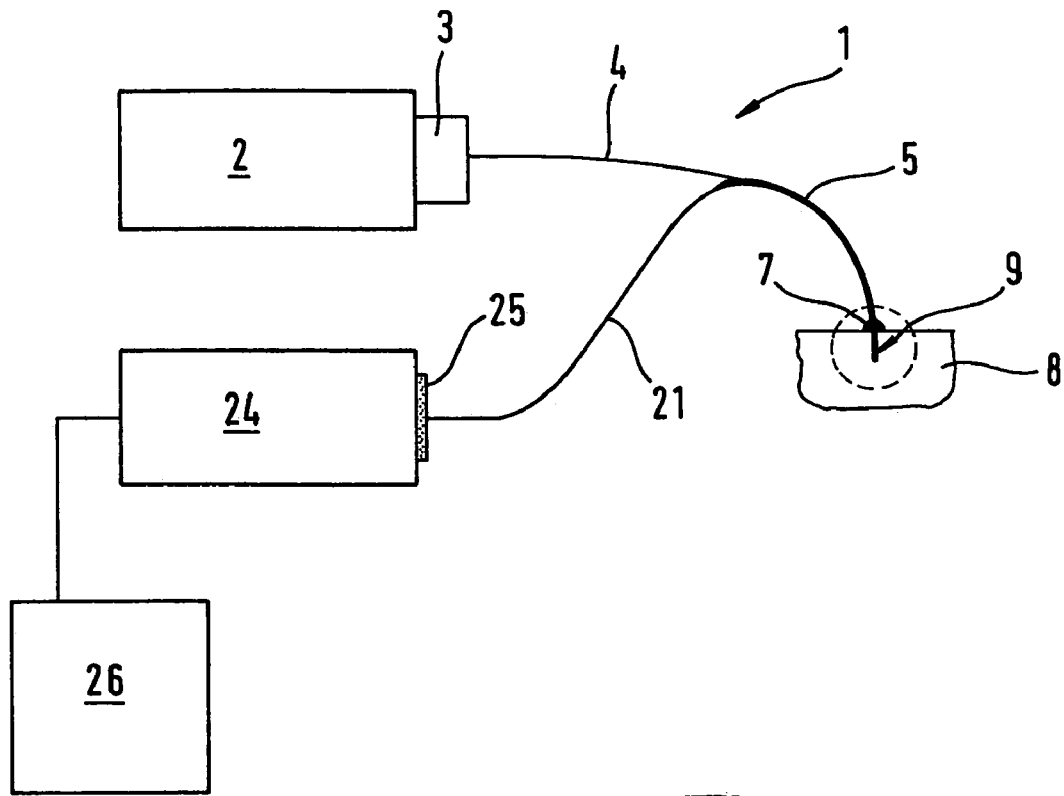
FIG. 1; shows a schematic diagram of the inventive analysis system.

FIG. 1 shows in a highly schematized diagram the essential components of an inventive analysis system designated on the whole by 1. The light source is a laser 2 (preferably a semiconductor laser) which emits visible light or light from the near infrared. The primary light generated by the light source 2 is coupled into an inbound light guide 4 through a coupling device 3. The inbound light guide 4 is formed for a part of its length by the central fiber of an optical fiber bundle 5 whose distal section is designed as a scattered-light percutaneous sensor 7 piercing through the skin surface and into the skin. The distal end of the percutaneous sensor which is inserted into the skin 8 is designated sensor head 9.

Figure 2:
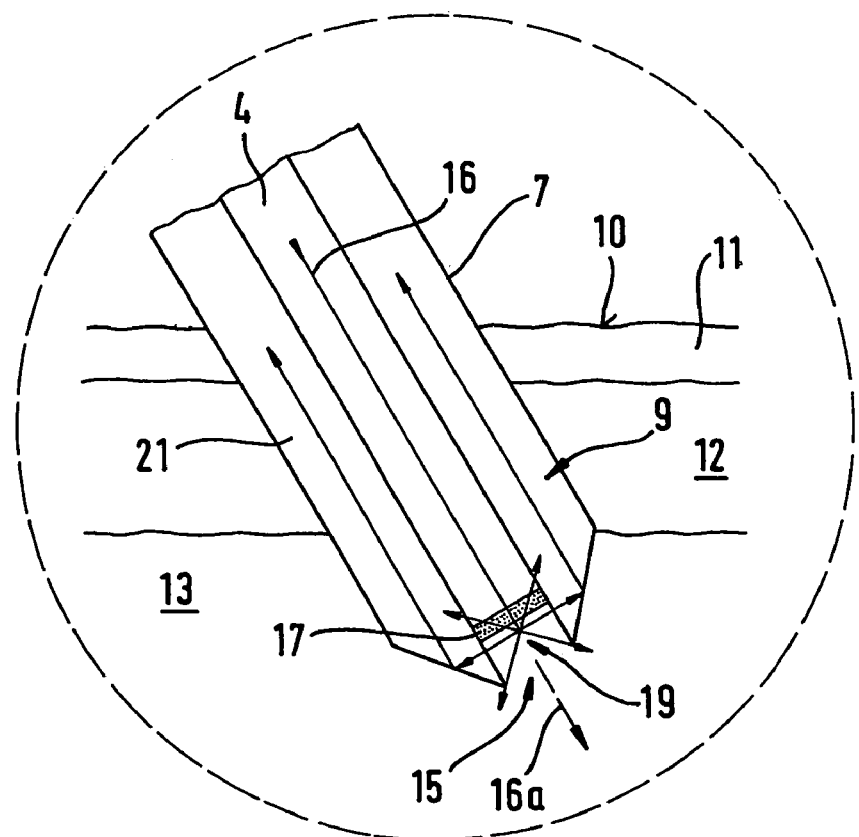
FIG. 2; shows an enlarged diagram of a detail from FIG. 1 in cross-section with a scattered-light percutaneous sensor inserted into the skin.

Details of the generation and detection of the Raman-scattered light are shown in FIG. 2 in an enlarged detail diagram which is also highly schematized. Further details may be taken from FIGS. 7 and 8. The sensor head 9 penetrates through the skin surface and the underlying layers of skin, namely the epidermis 11 and the dermis 12, into the subcutis 13 so that the test volume 15 contains interstitial fluid at the distal end of the sensor head in the direction of insertion.

The primary light passes through a light irradiation surface 18, which is formed by the distal end face of the inbound light guide 4, into the test volume 15. To eliminate Raman scattering and fluorescence occurring in the inbound light guide 4, it is provided with a bandpass filter, preferably on its most distal end, to ensure that the primary light penetrating into the test volume 15 has an extremely narrow bandwidth.

Due to scattering, the secondary light occurring in the test volume 15 contains Raman components as well as Rayleigh components and fluorescence components. A large portion of the scattered secondary light 19 penetrates through a light receiving surface 20 into a detection light guide 21 (see FIG. 7). In the preferred embodiment depicted here, the detection light guide 21 consists of a plurality of optical fibers 22 which are arranged at least on both sides of the inbound light guide 4.

This embodiment shows that the term "detection light guide" must not be interpreted in a restrictive sense as pertaining to a single fiber-optic element, in particular an optical fiber. Instead the term "detection light guide" refers to the totality of fiber-optic elements that serve in an inventive system to transport the scattered light from a light receiving surface 20 (which may consist of a plurality of partial surfaces) to the spectrometer. Consequently, the detection light guide may consist of a plurality of fiber-optic elements running in parallel as well as a plurality of fiber-optic elements arranged in succession, made of a suitable transparent material in which the detection light is transported. The same is also basically true for the inbound light guide, although this is, in the area of the sensor head, preferably formed by a single central optical fiber.

In the optical fibers 22 of the detection light guide 21 reflection takes place at a reflective surface 23 (see FIG. 7) which is inclined obliquely to the axis of the primary light 16. It runs on the side of the detection light guide 21 which faces away from the primary light beam 16a.

The detected secondary light is conducted in the detection light guide 21 to a wavelength-selective detection device 24 having at its input a notch filter (negated bandpass filter) which eliminates as much as possible of the wavelength of the primary light and thus the elastically scattered Rayleigh components of the secondary light. In the detection device 24 the detected light is divided spectrally and the resulting spectrum, which contains the information for determining the glucose concentration, is recorded digitally. The digitized spectrum is transmitted to an electronic analyzer device 26, e.g., a computer and is analyzed there. This is preferably done by means of a multivariate analysis method such as used in spectroscopy (e.g., principle component regression, partial least squares). Such methods are described, for example, in H. Martens et al., "Multivariate Calibration," John Wiley & Sons, New York, N.Y. 1989 A. Höskuldsson, "Prediction Methods in Science and Technology," Thor Publishing, Denmark 1996. Generation of primary light, spectral analysis of the secondary light and further analysis of the spectrum may be performed in separate parts. In a highly integrated portable analysis system, they are preferably integrated into a common instrument housing.

FIGS. 3 through 11 illustrate various preferred embodiments of the sensor head 9. The distal end of sensor head 9 is always enclosed by a semipermeable membrane 30 such that macromolecules having a molecular weight above the exclusion limit of the membrane cannot penetrate into the test volume 15 which is enclosed by the membrane 30. It has been found within the context of the present invention that through this measure, in particular taking into account the preferred values of the exclusion limit mentioned above, a significant reduction in the interfering fluorescence is achieved. This is true in particular in the preferred range of the primary light wavelength, i.e., in the visible and very near infrared portion of the spectrum. According to the test results by the present inventors, suppression of the fluorescence background is optimal in the spectral range between 550 and 750 nm, in particular between 570 and 650 nm.

With each of the embodiments depicted in FIGS. 3 through 11, measures were taken to increase the intensity of the Raman-scattered light detected by the detection light guide 21, in comparison with interfering light components, by means of a reflective surface.

Figure 3:
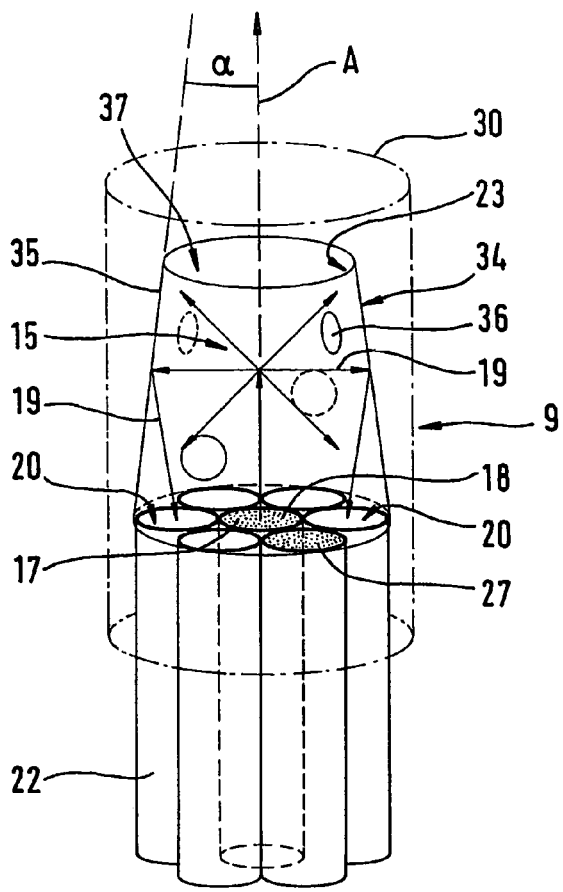
FIG. 3; shows a schematic perspective diagram of a sensor head.
Figure 4:
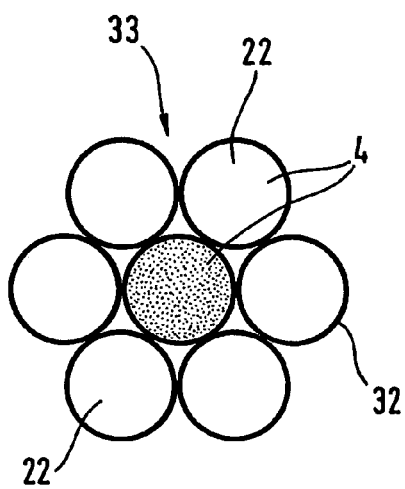
FIG. 4; shows a cross-section through the light guides of the sensor head shown in FIG. 3.

In the embodiments illustrated in FIGS. 3 and 4, the detection light guide 21 comprises six optical fibers 22 which are arranged in a ring pattern around a central optical fiber forming the inbound light guide 4. The totality of the optical fibers 22 thus forms a detection fiber-optical ring 33 which surrounds the central inbound light guide 4. All fibers are surrounded by cladding 32 (as is customary in fiber-optic technology) which has a lower refractive index than the fiber material. Therefore, the light transport in the fibers is achieved by total reflection in known manner and the fibers are optically separated from one another.

In the embodiment depicted in FIG. 3, the light receiving surface 20 of the detection light guide 21 is formed by the end faces of the optical fibers 22 running normal to the fiber axis ("flat face" arrangement). A reflective surface 23 is formed by the inside surface of a reflector element 34 which form a lateral limitation of the test volume 15 and is not part of the detection light guide 21. It is inclined at an angle $\alpha$ to the axis A of the primary light beam 16a emerging from the light irradiation surface 18 such that the scattered secondary light 19 is reflected in the direction of the light receiving surface 20 of the detection light guide 21, i.e., it penetrates to an increased extent into the detection light guide 21.

Figure 5:
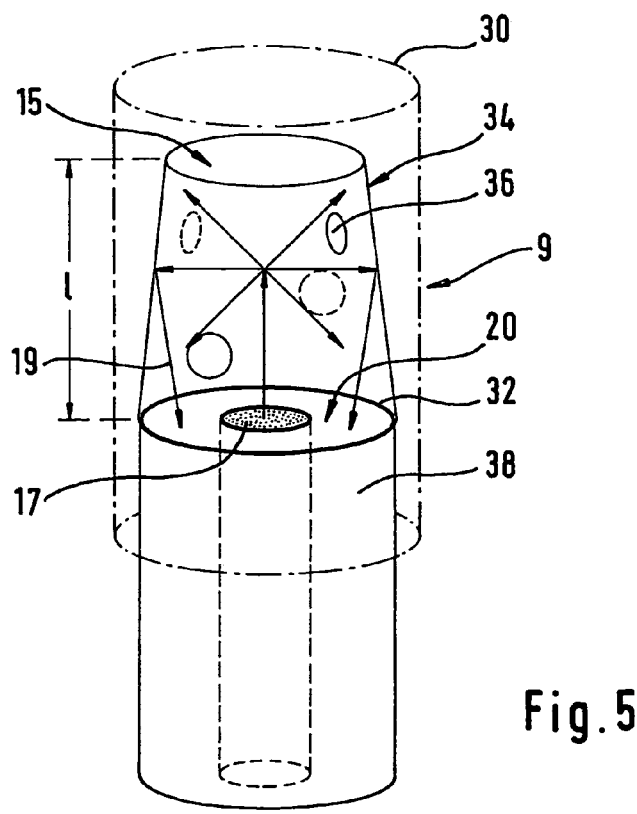
FIG. 5; shows a schematic perspective diagram of a second embodiment of a sensor head.

The reflector element 34 is in the preferred embodiment depicted in FIGS. 3 and 5 designed as a reflecting sleeve 35 which surrounds the primary light beam 16a and has slightly conically inclined side walls.

The reflector element 34 preferably consists completely of a thin film of a highly reflective metal such as gold. In principle, however, it may also be made of a material that is not itself reflective (such as a plastic) but has a reflective (metallic) coating—preferably on the inside facing the primary light beam 16a.

Holes 36 are provided in the wall of the reflecting sleeve 35 to improve the liquid exchange with the volume enclosed thereby—in addition to the distal sleeve opening 37 through which the primary light beam 16a penetrates. Again in this embodiment, suitable filter coatings are preferably provided, namely a bandpass filter 17 at the light irradiation surface 18 and a notch filter 27 on the light receiving surface 20 (for the sake of simplicity, shown only with one optical fiber 22 in FIG. 3).

Figure 6:
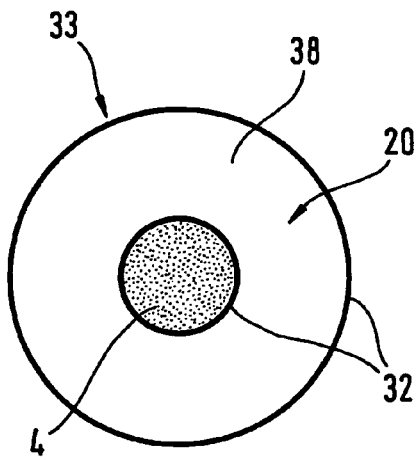
FIG. 6; shows a cross-section through the light guides of the sensor head depicted in FIG. 5.
Figure 11:
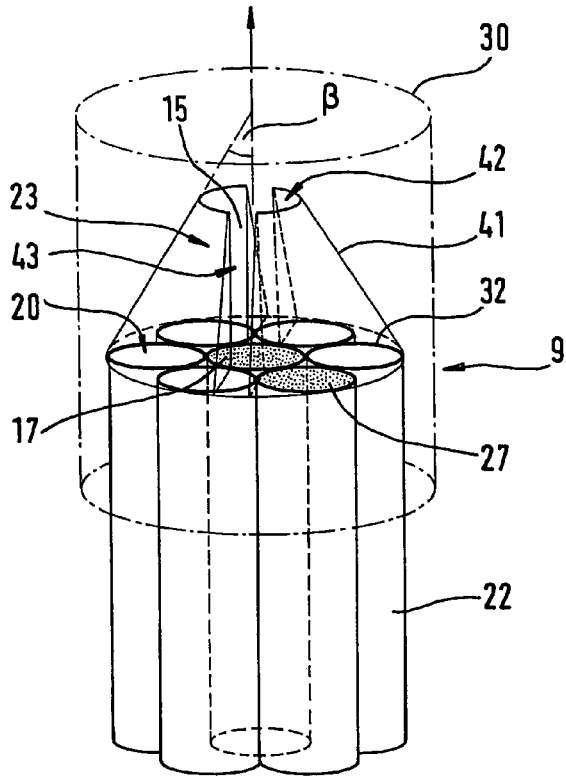
FIG. 11; shows a schematic perspective diagram of a fifth embodiment of a sensor head.

The embodiment depicted in FIGS. 5 and 6 differs from that of FIGS. 3 and 4 only in that the light guide ring 33 is not formed by a plurality of individual fibers 22 but instead by a fiber-optic tube 38. Thereby the light receiving surface is increased (at a given outside diameter) and the cross-section available for conducting the detection light is also increased. However, production is substantially more difficult than with the embodiment depicted in FIGS. 3 and 4.

The preferred dimensions of the reflecting sleeve 35. The angle of inclination α of the reflective surface 23 to the axis A of the primary light beam 16a should be very acute, with values of less than 10 degrees being preferred. The axial length of the reflecting sleeve is preferably between 1 mm and 20 mm, with values of 3 mm or 5 mm being preferred as the lower limit and 10 mm as the upper limit. The low inclination of the reflecting sleeve results in the test volume 15 extending forward beyond the distal sleeve opening 37. Therefore, the test volume 15 is large, so the detected Raman intensity is increased. The size of the test volume 15 is influenced in a positive sense by the fact that a thin-walled reflecting sleeve 35 is used, its proximal diameter (facing the detection light guide) approximately matching that of the connected section of the detection light guide. This maximizes the test volume which is possible at a given diameter of the sensor head 9.

FIGS. 7 through 11 have in common the fact that (as is also the case in FIG. 2) the reflective surface 23 is formed by an outer boundary surface 40 of the detection light guide 21 which surface faces away from the primary light beam 16a emerging from the light irradiation surface 18.

FIG. 7 shows the geometry according to FIG. 2 more clearly. The light receiving surface 20 of the detection light guide 21 is formed by lateral surfaces of the optical fibers 22 which run axially parallel and face the primary light beam 16a. The inbound light guide 4 is shorter than the detection light guide 21 so that the test volume 15 is rearwardly enclosed by the light irradiation surface 18 of the inbound light guide 4 and toward the sides it is enclosed by the light receiving surface 20 of the detection light guide 21. Here again, the aforementioned bandpass filters and notch filters 17 and 27 are provided. Filtering of the detection light is also improved by integrating an additional notch filter 39 into the detection light guide as close as possible to the light receiving surface 20.

In the variant depicted in FIGS. 9 and 10, the most distal end of the detection light guide 21 is formed by a transparent ring segment body 41 whose conical outside surface functions as a reflective surface 23. It has a central recess 42 which is aligned with the inbound light guide 4. The bordering wall of the recess 42 forms the light receiving surface 20 of the detection light guide 21 and encloses the test volume 15.

The term "ring segment body" in this context is understood to refer to a transparent body having a conical outside boundary surface 40 and a central recess of the type shown here. Its base surface 44 which faces the adjacent part of the detection light guide 22, is aligned with the detection light guide ring 33. The ring segment body must not be a complete truncated cone, however. Instead it is advantageous if, as shown here, it is interrupted to form a plurality of segments between which there are gaps forming liquid exchange openings 43 through which the liquid exchange between the test volume 15 and the space outside the ring segment body 41 is improved.

The desired reflection properties of the reflective surface 23 can be achieved, for example, by coating it with a cladding so that total reflection occurs on the boundary surface of the detection light guide 21. However, a metallic reflective coating on the boundary surface 40 forming the reflective surface 23 is preferred. According to a particularly preferred embodiment, the boundary surface 40 is coated with a filter coating 45 which reflects the Raman-scattered light but is permeable for the wavelength of the primary light. This improves the S/N ratio.

The embodiments depicted in FIGS. 9/10 and 11 differ (similarly to FIGS. 3/4 and 5/6) through the use of different types of light guide rings 33, namely a plurality of optical fibers 22 or a tubular fiber-optic element 38.

According to the investigations conducted in the context of the present invention, the angle of inclination β of the reflective surface 23 to the axis of the primary light beam 16a should preferably be between 10° and 40° in the embodiment depicted in FIGS. 7 through 11, where the reflective surface 23 is formed by an outer boundary surface of the detection light guide 21. The results of investigations of this type are depicted graphically in FIGS. 12 through 14.

Figure 12:
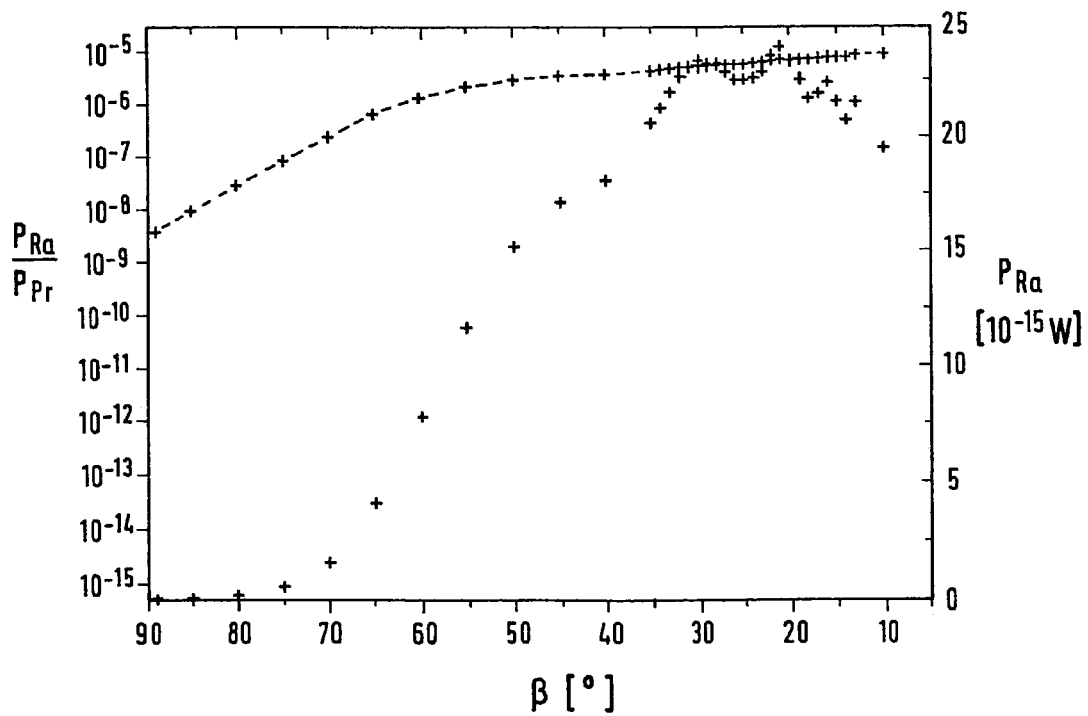
FIG. 12; shows a graphic plot of the absolute Raman intensity and the relative Raman intensity as a function of the angle of inclination of a reflective surface having filter properties provided on the sensor head.

FIG. 12 shows the results of simulation experiments for different measurement geometries, showing the dependence of the absolute Raman power $P_{RA}$ (right ordinate) on the angle β as a series of crosses (+) that are not connected, and the relationship of the Raman power $P_{RA}$ to the sum of the detected power of the incident light $P_{PR}$ (Rayleigh scattered and reflected primary light; left ordinate) as crosses (+) connected by a dotted line.

The results shown here are based on the measurement geometry according to FIG. 7, where the reflective surface is coated with a filter coating so that the Raman-scattered light is reflected on the reflective surface 23 but primary light is allowed to pass through. It can be seen here that very good results are achieved with regard to the absolute intensity of the Raman light as well as the ratio between $P_{RA}$ and $P_{PR}$ at relatively small angles, in particular between approx. 15° and approx. 35°.

As any person skilled in the art will recognize from the previous description and from the figures and claims, modifications and changes can be made to the preferred embodiment of the invention without departing from the scope of the invention as defined in the following claims.

What is claimed is:

1. A system for the reagent-free determination of the concentration of an analyte in living tissue of a patient, the system comprising:
   a light transmitter for generating monochromatic primary light having a wavelength of at least 550 nm and at most 900 nm;

a scattered-light percutaneous sensor adapted to be inserted through the skin surface into the skin, wherein a distal end of the percutaneous sensor has a sensor head, wherein a distal end of the sensor head is enclosed by a semipermeable membrane to define a test volume for containing interstitial fluid from the tissue, wherein the semipermeable membrane prevents admission of macromolecules having a molecular weight above the exclusion limit of the semipermeable membrane to the test volume;

an inbound light guide in which the primary light is conducted through the skin surface into the interior of the body;

a light irradiation surface formed at a distal end of the inbound light guide through which the primary light penetrates into the test volume;

a detection light guide which has at its distal end a light receiving surface through which a secondary light scattered in the test volume penetrates into the detection light guide, wherein the light irradiation surface of the inbound light guide and the light receiving surface of the detection light guide are adapted to be located subcutaneously so that the test volume contains the interstitial fluid;

a wavelength-sensitive detection device connected to the detection light guide for detection of Raman-scattered components of the secondary light; and an evaluation device for determining the concentration of the analyte from the Raman-scattered components of the secondary light.

2. The system according to claim 1, wherein the analyte is glucose.

3. The system according to claim 1, wherein the primary light is irradiated with only one wavelength, the wavelength being such that a spontaneous Raman scattering occurs.

4. The system according to claim 1, wherein the wavelength of the primary light is at most 800 nm.

5. The system according to claim 1, wherein a multivariate analysis method is used for determining the concentration of the analyte from the Raman spectrum.

6. The system according to claim 1, wherein the exclusion limit of the semipermeable membrane is at most 50 kDa.

7. The system according to claim 1, wherein the detection light guide is in the form of a ring which surrounds a central inbound light guide.

8. The system according to claim 7, wherein the detection light guide ring is formed by a plurality of optical fibers arranged in a ring pattern around the inbound light guide.

9. The system according to claim 7, wherein the detection light guide ring is formed by a fiber-optic tube which surrounds the inbound light guide.

10. The system according to claim 1, wherein the percutaneous sensor has a diameter of at most 2 mm.

11. The system according to claim 1, wherein the wavelength of the primary light is at most 600 nm.

12. The system according to claim 1, wherein the exclusion limit of the semipermeable membrane is at most 20 kDa.

13. The system according to claim 1, wherein the percutaneous sensor has a diameter of at most 1 mm.

14. The system according to claim 1, wherein the percutaneous sensor has a diameter of at most 0.5 mm.

15. The system according to claim 1, wherein:
the sensor head includes a reflective surface [configured and arranged] positioned around the test volume to reflect the Raman-scattered components of the secondary light towards the light receiving surface of the detection light guide; and the reflective surface is [designed and arranged]positioned to not reflect the primary light emitted from the inbound light guide towards the light receiving surface of the detection light guide.

16. A system for the reagent-free determination of the concentration of an analyte in living tissue of a patient, the system comprising:

a light transmitter for generating monochromatic primary light having a wavelength of at least 550 nm and at most 900 nm;

a scattered-light percutaneous sensor adapted to be inserted through the skin surface into the skin, wherein a distal end of the percutaneous sensor has a sensor head, the sensor head defining a test volume for containing interstitial fluid from the tissue;

an inbound light guide in which the primary light is conducted through the skin surface into the interior of the body;

a light irradiation surface formed at a distal end of the inbound light guide through which the primary light penetrates into the test volume;

a detection light guide which has at its distal end a light receiving surface through which a secondary light scattered in the test volume penetrates into the detection light guide, wherein the light inadiation surface of the inbound light guide and the light receiving surface of the detection light guide are adapted to be located subcutaneously so that the test volume contains the interstitial fluid;

a wavelength-sensitive detection device connected to the detection light guide for detection of Raman-scattered components of the secondary light;

an evaluation device for determining the concentration of the analyte from the Raman-scattered components of the secondary light;

wherein the sensor head includes a reflective surface positioned around the test volume to reflect the Raman-scattered components of the secondary light towards the light receiving surface of the detection light guide; and wherein the reflective surface is positioned to not reflect the primary light emitted from the inbound light guide towards the light receiving surface of the detection light guide.

17. The system according to claim 16, wherein the reflective surface is formed by a boundary surface of the detection light guide on the side of the detection light guide which faces away from the primary light beam emerging from the light irradiation surface.

18. The system according to claim 17, wherein the boundary surface is coated with a filter coating which allows the primary light to pass through but reflects the Raman-scattered light.

19. The system according to claim 17, wherein the reflective surface is inclined at an angle ($\beta$) between 10° and 40° to the axis (A) of the primary light beam emerging from the light inadiation surface.

20. The system according to claim 17, wherein the distal end of the detection light guide is designed as a transparent ring segment body having a conical reflective surface and a central recess, the recess being aligned with the inbound light guide.

21. The system according to claim 16, wherein the reflective surface is formed by a surface of a reflector element which forms a lateral limitation of the test volume and the reflective surface is inclined to the axis (A) of the primary light beam emerging from the light inadiation surface such that the scattered secondary light is concentrated towards the light receiving surface of the detection light guide.

22. The system according to claim 21, wherein the reflective surface is inclined at an angle ($\alpha$) of less than 10° to the axis (A) of the primary light beam emerging from the light irradiation surface.

23. The system according to claim 21, wherein the reflector element is a reflecting sleeve surrounding the primary light beam.

24. The system according to claim 16, wherein a distal end of the sensor head is enclosed by a semipermeable membrane.

25. A method, comprising:
inserting a sensor head of a scattered-light percutaneous sensor into skin, wherein the sensor head includes a light irradiation surface and a light receiving surface, wherein said inserting includes locating the light irradiation surface and the light receiving surface in subcutaneous connective tissue of the skin so that a test volume of the sensor head contains interstitial fluid, wherein the sensor head is enclosed by a semipermeable membrane to define the test volume;
shining a monochromatic primary light that has wavelength of at least 550 nm and at most 900 nm from the light irradiation surface of the sensor head into the test volume containing the interstitial fluid;
receiving a secondary light scattered from the test volume containing the interstitial fluid at the light receiving surface of the sensor head;
detecting Raman-scattered components of the secondary light from the secondary surface with a wavelength-sensitive detection device;
determining concentration of analyte in the test volume from the Raman-scattered components of the secondary light; and reducing fluorescence interference by preventing access of macromolecules that have a molecular weight greater than 50 kDa to the test volume with the semipermeable membrane of the sensor head.

26. The method of claim 25, further comprising:
suppressing the fluorescence interference by limiting the spectral range of the primary light between 550 nm and 750 nm during said shining.

27. The method of claim 25, wherein the analyte is non-fluorescing and has a molecular weight of at most 50 kDa.

28. The method of claim 25, wherein said determining the concentration of the analyte includes determining glucose concentration.

29. The method of claim 25, further comprising:
reducing interference from the primary light, wherein said reducing interference from the primary light includes
directing the primary light from the light irradiation surface through a recess in a reflector of the sensor head, and
reflecting the secondary light scattered from the test volume with the reflector to the wavelength-sensitive detection device.

30. The method of claim 25, wherein said determining the concentration of the analyte includes multivariate analysis.

31. The method of claim 25, wherein:
the analyte is glucose; and
said determining includes determining glucose levels by conventional Raman spectroscopy.

32. The method of claim 25, providing a readout of the concentration.

* * * * *

UNITED STATES PATENT AND TRADEMARK OFFICE
CERTIFICATE OF CORRECTION

PATENT NO. : 7,277,740 B2  
APPLICATION NO. : 10/800215  
DATED : October 2, 2007  
INVENTOR(S) : Daniel Rohleder et al.

Page 1 of 1

It is certified that error appears in the above-identified patent and that said Letters Patent is hereby corrected as shown below:

Column 11, lines 66-67, please delete "[configured and arranged]"

Column 12, line 4, please delete "[design and arranged]"

Column 12, line 60, please change "inadiation" to --irradiation--

Column 13, line 3, please change "inadiation" to --irradiation--

Signed and Sealed this

Eighteenth Day of December, 2007

JON W. DUDAS  
*Director of the United States Patent and Trademark Office*